US009387184B2

(12) United States Patent
Hansen et al.

(10) Patent No.: US 9,387,184 B2
(45) Date of Patent: *Jul. 12, 2016

(54) PHARMACEUTICAL COMPOSITIONS FOR COMBINATION THERAPY

(71) Applicant: Saniona A/S, Ballerup (DK)

(72) Inventors: Henrik Bjork Hansen, Kobenhavn N (DK); Morten Grunnet, Kobenhavn O (DK); Bo Hjorth Bentzen, Espergaerde (DK); Lars Hyveled-Nielsen, Lyngby (DK); Jorgen Buus Lassen, Bagsvaerd (DK); Claus Sundgreen, Frederiksberg (DK)

(73) Assignee: Saniona A/S, Ballerup (DK)

( * ) Notice: Subject to any disclaimer, the term of this patent is extended or adjusted under 35 U.S.C. 154(b) by 0 days.

This patent is subject to a terminal disclaimer.

(21) Appl. No.: 14/936,963

(22) Filed: Nov. 10, 2015

(65) Prior Publication Data

US 2016/0074344 A1    Mar. 17, 2016

Related U.S. Application Data

(63) Continuation of application No. 14/379,032, filed as application No. PCT/EP2013/052941 on Feb. 14, 2013, now Pat. No. 9,211,271.

(60) Provisional application No. 61/599,623, filed on Feb. 16, 2012.

(30) Foreign Application Priority Data

Feb. 16, 2012    (DK) .................................. 2012 70076

(51) Int. Cl.
*A61K 31/138*    (2006.01)
*A61K 31/46*    (2006.01)

(52) U.S. Cl.
CPC ............... *A61K 31/138* (2013.01); *A61K 31/46* (2013.01)

(58) Field of Classification Search
CPC ....... A61K 31/38; A61K 31/46; A61K 31/138
USPC .......................................................... 514/304
See application file for complete search history.

(56) References Cited

U.S. PATENT DOCUMENTS

2015/0025107 A1*    1/2015    Hansen ................ A61K 31/135
                                                             514/304

FOREIGN PATENT DOCUMENTS

| DK | WO 2009080693 A2 * | 7/2009 | ............ A61K 31/46 |
|----|---|---|---|
| WO | WO 92/16197 A1 | 10/1992 | |
| WO | WO 97/30997 A1 | 8/1997 | |
| WO | WO 2005/070427 A1 | 8/2005 | |
| WO | WO 2009/065845 A1 | 5/2009 | |
| WO | WO 2009/080691 A2 | 7/2009 | |
| WO | WO 2009/080693 A2 | 7/2009 | |
| WO | WO 2011/100659 A2 | 8/2011 | |

OTHER PUBLICATIONS

Astrup et al., "Effect of tesofensine on bodyweight loss, body composition, and quality of life in obese patients: a randomized, double-blind, placebo-controlled trial", The Lancet, Nov. 29, 2008, vol. 372, No. 9653, pp. 1906-1913.
Astrup et al., "Weight Loss Produced by Tesofensine in patients With Parkinson's or Alzheimer's Disease", Obesity, Jun. 1, 2008, vol. 16, No. 6, pp. 1363-1369.
International Patent Application No. PCT/EP2013/052941: International Search Report dated May 2, 2013, 3 pages.
Messerli et al., "Body Weight Changes with β-Blocker Use: Results from Gemini", The American Journal of Medicine, Jul. 2007, 120, pp. 610-615.

* cited by examiner

*Primary Examiner* — Kristin Vajda
(74) *Attorney, Agent, or Firm* — Baker & Hostetler LLP

(57) ABSTRACT

This invention relates to the use of pharmaceutical compositions comprising a therapeutically effective combination of Tesofensine and Metoprolol for preventing the cardiovascular side effects of Tesofensine, while leaving the robust inhibitory efficacy on food intake and body weight loss unaffected.

14 Claims, 24 Drawing Sheets

PHARMACEUTICAL COMPOSITIONS FOR COMBINATION THERAPY

CROSS-REFERENCE TO RELATED APPLICATIONS

This application is a continuation of U.S. patent application Ser. No. 14/379,032, filed Aug. 15, 2014, which is the national stage entry of International Patent Application No. PCT/EP2013/052941, filed Feb. 14, 2013, which claims the benefit of priority to U.S. Provisional Patent Application No. 61/599,623, filed Feb. 16, 2012, the entireties of which are incorporated herein by reference.

TECHNICAL FIELD

This invention relates to the use of pharmaceutical compositions comprising a therapeutically effective combination of Tesofensine and Metoprolol for preventing the cardiovascular side effects of Tesofensine, while leaving the robust inhibitory efficacy on food intake and body weight loss unaffected.

BACKGROUND ART

Within the past decades the prevalence of obesity has risen in virtually all ethnic, racial and socioeconomic populations, in both genders and in all age groups. Obesity is associated with a significantly elevated risk for type 2 diabetes, coronary heart diseases, hypertension and numerous other major illnesses and overall mortality from all causes. Therefore, weight reduction is critical for the obese patient. Thus there is impetus for creating new and alternative treatments for management of obesity.

Tesofensine, i.e. (1R,2R,3S,5S)-3-(3,4-dichlorophenyl)-2-(ethoxymethyl)-8-methyl-8-azabicyclo[3.2.1]octane], first described in WO 97/30997, is a triple monoamine reuptake inhibitor in development for the treatment of obesity.

WO 2005/070427 describes the use of certain monoamine neurotransmitter re-uptake inhibitors for obtaining a sustained reduction of body weight. WO 2009/065845 describes the use of certain monoamine neurotransmitter re-uptake inhibitors for the treatment of over-eating disorders. WO 2009/080691 describes the use of certain monoamine neurotransmitter re-uptake inhibitors in a combination with additional anti-obesity agents for the treatment of obesity.

Tesofensine effectively produces a weight loss in obese individuals of about twice of that seen with currently marketed anti-obesity drugs. Results from clinical studies with Tesofensine also showed that the compound has a good safety profile and is well tolerated. However, though no clinically relevant cardiovascular adverse events or changes in either blood pressure or pulse were seen, some cardiovascular effects were measured with slight increases in heart rate and trends in blood pressure. Although such small effects have no immediate risk to the patient, some medical and regulatory concerns have been raised based on observational studies, that even small changes in cardiovascular parameters may have long term implications on patients' benefit/risk evaluation.

Preclinical and clinical data suggest that appetite suppression is an important mechanism by which Tesofensine exerts its robust weight reducing effect. Notably, the strong hypophagic response (i.e. less appetite, decreased feeding) to Tesofensine treatment is demonstrated to be linked to central stimulation of noradrenergic and dopaminergic neurotransmission. However, the sympathomimetic mode of action of Tesofensine may also associate with the elevated heart rate and blood pressure observed in clinical settings.

WO 2009/080693 describes pharmaceutical compositions comprising certain monoamine neurotransmitter re-uptake inhibitors in a combination with certain beta blockers, and WO 2011/100659 describes a method for ameliorating drug-induced elevation of blood pressure or increase in heartbeat by administration of an antihypertensive drug.

As such combination therapies seem tempting, drug combinations of Tesofensine with antihypertensive agents representing different mechanisms of action have been investigated. Based on these experiments it was found that some antihypertensive agents actually happen to interfere with the anti-obesity effects of Tesofensine, and thus are not suited for such combination therapy. Moreover, other antihypertensive agents are actually unable to reverse the increase in systolic blood pressure and heart rate induced by Tesofensine.

Metoprolol, i.e. 1-(Isopropylamino)-3-[4-(2-methoxyethyl)-phenoxy]-propan-2-ol, branded under various trade names, is a selective β1 (adrenergic) receptor blocker normally used in the treatment of various disorders of the cardiovascular system, and in particular hypertension.

SUMMARY OF THE INVENTION

It has now surprisingly been found that the use of Metoprolol, in a specific combination therapy with Tesofensine, for the treatment of obesity, shows promising results in terms of preventing the cardiovascular effects induced Tesofensine, while leaving the robust inhibitory efficacy of Tesofensine on food intake and body weight loss unaffected.

Therefore, in one aspect, the invention provides a method of treatment, prevention or alleviation of obesity, or an obesity associated disorder, and for treatment, prevention or alleviation of the cardiovascular side effects of Tesofensine, in a living animal body, including a human, which method comprises the step of administering to such a living animal body in need thereof, a therapeutically effective amount of Tesofensine, or a pharmaceutically acceptable salt thereof; in a combination therapy with Metoprolol, or a pharmaceutically acceptable salt thereof.

In another aspect the invention provides a combination of Tesofensine, or a pharmaceutically acceptable salt thereof, and Metoprolol, or a pharmaceutically acceptable salt thereof, the treatment, prevention or alleviation of obesity, or an obesity associated disorder, and for treatment, prevention or alleviation of the cardiovascular side effects of Tesofensine.

In a third aspect the invention provides a combination of Tesofensine, or a pharmaceutically acceptable salt thereof, and Metoprolol, or a pharmaceutically acceptable salt thereof, for use as a medicament.

In a fourth aspect the invention provides a combination of Tesofensine, or a pharmaceutically acceptable salt thereof; and Metoprolol, or a pharmaceutically acceptable salt thereof; for the treatment, prevention or alleviation of obesity, or an obesity associated disorder, and for treatment, prevention or alleviation of the cardiovascular side effects of Tesofensine, in a mammal, including a human.

In a fifth aspect the invention relates to the use of a combination of Tesofensine, or a pharmaceutically acceptable salt thereof; and Metoprolol, or a pharmaceutically acceptable salt thereof; for the manufacture of a medicament for the treatment, prevention or alleviation of obesity, or an obesity associated disorder, and for treatment, prevention or alleviation of the cardiovascular side effects of Tesofensine, in a mammal, including a human.

In a sixth aspect the invention provides a pharmaceutical composition comprising Tesofensine, or a pharmaceutically acceptable salt thereof, for use in a combination therapy together with a pharmaceutical composition comprising Metoprolol, or a pharmaceutically acceptable salt thereof, for the treatment, prevention or alleviation of obesity, or an obesity associated disorder, and for treatment, prevention or alleviation of the cardiovascular side effects of Tesofensine.

In an eight aspect the invention provides a pharmaceutical composition comprising a therapeutically effective amount of Tesofensine, or a pharmaceutically acceptable salt thereof, and a therapeutically effective amount of Metoprolol, or a pharmaceutically acceptable salt thereof, together with one or more adjuvants, excipients, carriers and/or diluents.

In a ninth aspect the invention provides a kit of parts comprising at least two separate unit dosage forms (A) and (B), wherein (A) comprises Tesofensine, or a pharmaceutically acceptable salt thereof; and (B) comprises Metoprolol, or a pharmaceutically acceptable salt thereof; and optionally (C) instructions for the simultaneous, sequential or separate administration of the Tesofensine of (A) and the Metoprolol of (B), to a patient in need thereof.

Other objects of the invention will be apparent to the person skilled in the art from the following detailed description and examples.

BRIEF DESCRIPTION OF THE DRAWINGS

The present invention is further illustrated by reference to the accompanying drawing, in which:

FIG. 1A depicts mean cumulative food intake (2 hour intervals) measured over 48 hours after acute dosing of tesofensine or saline vehicle. FIG. 1B depicts mean food intake measured over 48 hours, averaged in the 12 hours dark and light phase intervals, respectively. FIGS. 1C and 1D depict net body weight gain given relative (%) and absolute values (grams), respectively, compared to body weight measured prior to dosing on day 0. FIG. 1E depicts mean locomotor activity measured over 48 hours, averaged in the corresponding 12 hours dark and light phase intervals, respectively. Dark and white horizontal bars below the x-axis indicate 12 hours dark and light phases, respectively. Abbreviations: VEH, vehicle; TESO, tesofensine. $*p<0.05$, $p<0.01$, $*p<0.001$ (compared to VEH)];

FIG. 2A depicts mean heart rate±S.E.M. averaged in 12 hours intervals. FIG. 2B depicts mean diastolic blood pressure averaged in 12 hours intervals. FIG. 2C depicts mean systolic blood pressure averaged in 12 hours intervals. Dark and white horizontal bars below the x-axis indicate 12 hours dark and light phases, respectively. Abbreviations: VEH, vehicle; TESO, tesofensine; bpm, beats per minute. $*p<0.05$, $p<0.01$, $*p<0.001$ (compared to VEH)];

FIG. 3A depicts mean cumulative food intake (2 hours intervals) measured over 48 hours after acute administration of Metoprolol+Tesofensine combinations or saline vehicle. FIG. 3B depicts mean food intake measured over 48 hours, averaged in the 12 hours dark and light phase intervals, respectively. FIGS. 3C and 3D depict net body weight gain given in relative (%) and absolute values (grams) compared to body weight measured prior to dosing on day 0. FIG. 3E depicts mean locomotor activity measured over 48 hours, averaged in the 12 hours dark and light phase intervals, respectively. Dark and white horizontal bars below the x-axis indicate 12 hours dark and light phases, respectively. Abbreviations: VEH, vehicle, TESO, tesofensine; MET, Metoprolol. $p<0.01$, $*p<0.001$ (compared to VEH+VEH); $^{\#}p<0.05$, $^{\#\#}p<0.01$ (compared to VEH+TESO 3.0)];

FIG. 4A depicts mean heart rate±S.E.M. averaged in 12 hours intervals. FIG. 4B depicts mean diastolic blood pressure averaged in 12 hours intervals. FIG. 4C depicts mean systolic blood pressure averaged in 12 hours intervals. Dark and white horizontal bars below the x-axis indicate 12 hours dark and light phases, respectively. Abbreviations: VEH, vehicle; TESO, tesofensine; MET, Metoprolol. $p<0.01$, $*p<0.001$ (compared to VEH+VEH); $^{\#}p<0.05$, $^{\#\#}p<0.01$, $^{\#\#\#}p<0.001$ (compared to VEH+TESO 3.0)];

FIG. 5A depicts mean cumulative food intake (2 hours intervals) measured over 48 hours after acute administration of Telmisartan+Tesofensine combinations or saline vehicle. FIG. 5B depicts mean food intake measured over 48 hours, averaged in the 12 hours dark and light phase intervals, respectively. FIGS. 5C and 5D depict net body weight gain given in relative (%) and absolute values (grams) compared to body weight measured prior to dosing on day 0. FIG. 5E depicts mean locomotor activity measured over 48 hours, averaged in the 12 hours dark and light phase intervals, respectively. Dark and white horizontal bars below the x-axis indicate 12 hours dark and light phases, respectively. Abbreviations: VEH, vehicle; TESO, tesofensine; TEL, Telmisartan. $*p<0.05$, $p<0.01$, $*p<0.001$ (compared to VEH+VEH)]; FIG. 6A depicts mean heart rate±S.E.M. averaged in 12 hours intervals. FIG. 6B depicts mean diastolic blood pressure averaged in 12 hours intervals. FIG. 6C depicts mean systolic blood pressure averaged in 12 hours intervals. Dark and white horizontal bars below the x-axis indicate 12 hours dark and light phases, respectively. Dark and white horizontal bars below the x-axis indicate 12 hours dark and light phases, respectively. Abbreviations: VEH, vehicle; TESO, tesofensine; TEL, Telmisartan. $*p<0.05$, $p<0.01$, $*p<0.001$ (compared to VEH+VEH); $^{\#}p<0.05$ (compared to VEH+TESO 3.0)].

DETAILED DISCLOSURE OF THE INVENTION

Figure 1A:
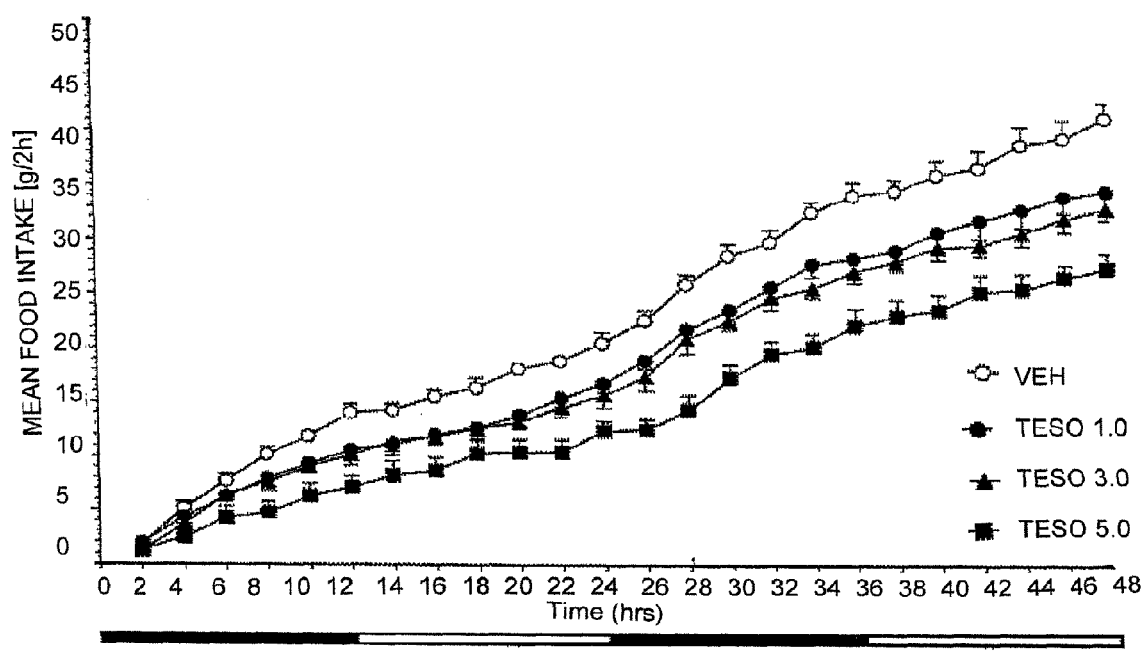
FIGS. 1A-1E show that Tesofensine (given 1.0-5.0 mg/kg, p.o.) dose-dependently inhibits food intake, reduces body weight, and stimulates locomotor activity in telemetrized rats.

Tesofensine is a centrally acting triple monoamine reuptake inhibitor (MRI) with intrinsic inhibitory activity on noradrenaline, serotonin and dopamine transporter function. When corrected for placebo and diet effects, long-term Tesofensine treatment produces a weight loss of about 10% in obese patients, which is twice as much as that achieved by currently marketed anti-obesity drugs.

The anti-obesity effect of Tesofensine is likely explained by dose-dependent hypophagia due to stimulation of satiety, suggesting that Tesofensine acts as an appetite suppressant to produce a negative energy balance. In addition, Tesofensine is also demonstrated to increase nocturnal energy expenditure in human subjects. These findings have recently been corroborated and extended in preclinical settings, demonstrating that Tesofensine induces a robust and sustained weight loss in a rat model of diet-induced obesity (DIO) of which the long-lasting drop in body weight is caused by appetite suppression with a gradually increase in energy expenditure. Notably, the hypophagic effect of Tesofensine in DIO rats is critically dependent on stimulated α1 adrenoceptor activity, and to a less extend dopamine D1 receptor function, indicating that enhancement of central noradrenergic and dopaminergic neurotransmission constitute important mechanisms underlying the robust appetite-suppressing effect of Tesofensine.

Overall, chronic Tesofensine treatment is associated with minor adverse events, and with minimal cardiovascular effects, suggesting that Tesofensine may be a well-tolerated long-term treatment for obesity. However, in this regard, dose-dependent elevations in heart rate and significant increases in blood pressure at the highest dose tested have been reported in obese individuals. We therefore speculated whether the sympathomimetic effects of Tesofensine might also associate with the reported effects on cardiovascular function.

To address this hypothesis, we simultaneously monitored effects on food intake and body weight regulation in conjunction with cardiovascular parameters in telemetrized (i.e. spontaneously hypertensive) rats following administration of Tesofensine alone, or in drug combinations of Tesofensine with antihypertensive agents representing different mechanisms of action, i.e. Metoprolol (i.e. a β1 adrenoceptor antagonist) and Telmisartan (i.e. an angiotension AT1 receptor antagonist).

It has now surprisingly been found that use of Metoprolol, in a specific combination therapy with Tesofensine, for the treatment of obesity or obesity associated disorders, shows promising results in terms of preventing the cardiovascular effects induced Tesofensine, while leaving the robust inhibitory efficacy of Tesofensine on food intake and body weight loss unaffected.

Therefore, in one aspect, the present invention relates to a combination therapy using Tesofensine and Metoprolol for the treatment, prevention or alleviation of obesity or an obesity associated disorder in a subject suffering from such disorders.

In another aspect the invention relates to the of a combination of Tesofensine, or a pharmaceutically acceptable salt thereof; and Metoprolol, or a pharmaceutically acceptable salt thereof; for the manufacture of a medicament for the treatment, prevention or alleviation of obesity, or an obesity associated disorder, and for treatment, prevention or alleviation of the cardiovascular side effects of Tesofensine, in a mammal, including a human.

Obesity and Obesity Associated Disorders

Obesity is a medical condition in which excess body fat has accumulated to the extent that it may have an adverse effect on health, leading to reduced life expectancy and/or increased health problems. Body mass index (BMI), a measurement which compares weight and height, defines people as over-weight (pre-obese) if their BMI is between 25 and 30 kg/m$^2$, and obese when it is greater than 30 kg/m$^2$.

In a preferred embodiment, the combination therapy according to the invention is contemplated useful for the treatment of pre-obese subjects, i.e. having a BMI between 25 and 30 kg/m$^2$.

In another preferred embodiment, the combination therapy according to the invention is contemplated useful for the treatment of obese subjects, i.e. having a BMI of above 30 kg/m$^2$.

In a third preferred embodiment, the combination therapy according to the invention is contemplated useful for the treatment of morbid obese subjects, i.e. having a BMI of above 35 kg/m$^2$.

In the context of this invention an obesity associated disorder is a disorder or condition selected from the group consisting of over-eating disorders, bulimia nervosa, binge eating disorder, compulsive over-eating, impaired appetite regulation, metabolic syndrome, type 2 diabetes, dyslipidemia, atherosclerosis and drug-induced obesity, e.g. following therapy with antidepressive or antipsychotic drugs.

Pharmaceutically Acceptable Salts

The active compounds for use according to the invention may be provided in any form suitable for the intended administration. Suitable forms include pharmaceutically (i.e. physiologically) acceptable salts, and pre- or prodrug forms of the compound of the invention.

Examples of pharmaceutically acceptable addition salts include, without limitation, the non-toxic inorganic and organic acid addition salts such as the hydrochloride, the hydrobromide, the nitrate, the perchlorate, the phosphate, the sulphate, the formate, the acetate, the aconate, the ascorbate, the benzenesulphonate, the benzoate, the cinnamate, the citrate, the embonate, the enantate, the fumarate, the glutamate, the glycolate, the lactate, the maleate, the malonate, the mandelate, the methanesulphonate, the naphthalene-2-sulphonate, the phthalate, the salicylate, the sorbate, the stearate, the succinate, the tartrate, the toluene-p-sulphonate, and the like. Such salts may be formed by procedures well known and described in the art.

Examples of pharmaceutically acceptable cationic salts of a chemical compound of the invention include, without limitation, the sodium, the potassium, the calcium, the magnesium, the zinc, the aluminium, the lithium, the choline, the lysinium, and the ammonium salt, and the like, of a chemical compound of the invention containing an anionic group. Such cationic salts may be formed by procedures well known and described in the art.

In the context of this invention the "onium salts" of N-containing compounds are also contemplated as pharmaceutically acceptable salts. Preferred "onium salts" include the alkyl-onium salts, the cycloalkyl-onium salts, and the cycloalkylalkyl-onium salts.

Examples of pre- or prodrug forms of the chemical compound for use according to the invention include examples of suitable prodrugs of the substances for use according to the invention include compounds modified at one or more reactive or derivatizable groups of the parent compound. Of particular interest are compounds modified at a carboxyl group, a hydroxyl group, or an amino group. Examples of suitable derivatives are esters or amides.

The chemical compounds for use according to the invention may be provided in dissoluble or indissoluble forms together with a pharmaceutically acceptable solvent such as water, ethanol, and the like. Dissoluble forms may also include hydrated forms such as the monohydrate, the dihydrate, the hemihydrate, the trihydrate, the tetrahydrate, and the like. In general, the dissoluble forms are considered equivalent to indissoluble forms for the purposes of this invention.

Pharmaceutical Compositions

In another aspect the invention relates to a combination of Tesofensine, or a pharmaceutically acceptable salt thereof, and Metoprolol, or a pharmaceutically acceptable salt thereof, for use as a medicament.

In a further aspect the invention provides pharmaceutical compositions comprising Tesofensine, or a pharmaceutically acceptable salt thereof, for use in a combination therapy together with a pharmaceutical composition comprising Metoprolol, or a pharmaceutically acceptable salt thereof, for the treatment, prevention or alleviation of obesity, or an obesity associated disorder, and for treatment, prevention or alleviation of the cardiovascular side effects of Tesofensine.

In a yet further aspect the invention provides pharmaceutical compositions comprising a therapeutically effective amount of Tesofensine, or a pharmaceutically acceptable salt thereof, and a therapeutically effective amount of Metoprolol, or a pharmaceutically acceptable salt thereof, together with one or more adjuvants, excipients, carriers and/or diluents.

While the compounds for use according to the invention may be administered in the form of the raw compound, it is preferred to introduce the active ingredients, optionally in the form of physiologically acceptable salts, in a pharmaceutical composition together with one or more adjuvants, excipients, carriers, buffers, diluents, and/or other customary pharmaceutical auxiliaries.

In a preferred embodiment, the invention provides pharmaceutical compositions comprising the active compounds or pharmaceutically acceptable salts or derivatives thereof, together with one or more pharmaceutically acceptable carriers therefore, and, optionally, other therapeutic and/or prophylactic ingredients, know and used in the art. The carrier(s) must be "acceptable" in the sense of being compatible with the other ingredients of the formulation and not harmful to the recipient thereof.

The pharmaceutical composition of the invention may be administered by any convenient route, which suits the desired therapy. Preferred routes of administration include oral administration, in particular in tablet, in capsule, in dragé in powder, or in liquid form, and parenteral administration, in particular cutaneous, subcutaneous, intramuscular, or intravenous injection. The pharmaceutical composition of the invention can be manufactured by the skilled person by use of standard methods and conventional techniques appropriate to the desired formulation. When desired, compositions adapted to give sustained release of the active ingredient may be employed.

Further details on techniques for formulation and administration may be found in the latest edition of *Remington's Pharmaceutical Sciences* (Maack Publishing Co., Easton, Pa.).

The dosage of the compound of Formula I is determined as the API (Active Pharmaceutical Ingredient), i.e. calculated as the free base. The actual dosage of each of the active ingredients depends on the nature and severity of the disease being treated, the exact mode of administration, form of administration and is within the discretion of the physician, and may be varied by titration of the dosage to the particular circumstances of this invention to produce the desired therapeutic effect.

It is currently believed that a daily dosage of Tesofensine in the range of from about 0.1 to about 1 mg active ingredient, preferably of from about 0.1 to about 0.5 mg active ingredient, is suitable for therapeutic treatments. The daily dosage of Tesofensine may be administered in one or several doses, such as two, per day. In one embodiment, the daily dosage is administered in one dose.

The daily dosage of Metoprolol is presently contemplated to be in the range of from about 25 to about 200 mg of active ingredient, preferably of from about 25 to about 100 mg active ingredient. The daily dosage of Metoprolol may be administered in one or several doses, such as two, per day. In one embodiment, the daily dosage is administered in one dose.

Pharmaceutical Kits of Parts

According to the invention there is also provided a kit of parts comprising at least two separate unit dosage forms (A) and (B), wherein (A) comprises Tesofensine, or a pharmaceutically acceptable salt thereof; and (B) comprises Metoprolol, or a pharmaceutically acceptable salt thereof; and optionally (C) instructions for the simultaneous, sequential or separate administration of the Tesofensine of (A) and the Metoprolol of (B), to a patient in need thereof.

Tesofensine for use according to the invention and Metoprolol for use according to the invention may preferably be provided in a form that is suitable for administration in conjunction with the other. This is intended to include instances where one or the other of two formulations may be administered (optionally repeatedly) prior to, after, and/or at the same time as administration with the other component.

Also Tesofensine for use according to the invention and Metoprolol for use according to the invention may be administered in a combined form, or separately or separately and sequentially, wherein the sequential administration is close in time or remote in time. This may in particular include that two formulations are administered (optionally repeatedly) sufficiently closely in time for there to be a beneficial effect for the patient, that is greater over the course of the treatment of the relevant condition than if either of the two formulations are administered (optionally repeatedly) alone, in the absence of the other formulation, over the same course of treatment. Determination of whether a combination provides a greater beneficial effect in respect of, and over the course of treatment of, a particular condition, will depend upon the condition to be treated or prevented, but may be achieved routinely by the person skilled in the art.

When used in this context, the terms "administered simultaneously" and "administered at the same time as" include that individual doses of Tesofensine and are administered within 48 hours, e.g. 24 hours, of each other.

Bringing the two components into association with each other, includes that components (A) and (B) may be provided as separate formulations (i.e. independently of one another), which are subsequently brought together for use in conjunction with each other in combination therapy; or packaged and presented together as separate components of a "combination pack" for use in conjunction with each other in combination therapy.

Methods of Therapy

In another aspect the invention provides methods of treatment, prevention or alleviation of obesity or an obesity associated disease of a living animal body, including a human, which method comprises the step of administering to such a living animal body in need thereof, a therapeutically effective amount of a combination of Tesofensine, or a pharmaceutically acceptable salt thereof, and Metoprolol, a pharmaceutically acceptable salt thereof.

In a preferred embodiment the obesity associated disorder is a disorder or condition selected from the group consisting of over-eating disorders, bulimia nervosa, binge eating disorder, compulsive over-eating, impaired appetite regulation, metabolic syndrome, type 2 diabetes, dyslipidemia, atherosclerosis and drug-induced obesity.

It is currently believed that a daily dosage of Tesofensine in the range of from about 0.1 to about 1 mg active ingredient, preferably of from about 0.1 to about 0.5 mg active ingredient, is suitable for therapeutic treatments. The daily dosage of Tesofensine may be administered in one or several doses, such as two, per day. In one embodiment, the daily dosage is administered in one dose.

The daily dosage of Metoprolol is presently contemplated to be in the range of from about 25 to about 200 mg of active ingredient, preferably of from about 25 to about 100 mg active ingredient. The daily dosage of Metoprolol may be administered in one or several doses, such as two, per day. In one embodiment, the daily dosage is administered in one dose.

EXAMPLES

The invention is further illustrated with reference to the following example, which is not intended to be in any way limiting to the scope of the invention as claimed.

Animal Care and Housing

Five months-old male normotensive Sprague-Dawley rats (508±18 g, Harlan, Horst, The Netherlands) were housed in solid bottomed Plexiglas cages with dust free wood chippings and a cardboard tube. Holding rooms were maintained under a 12-h light/dark cycle (lights off: 1500 h). Ambient temperature was 18.0 to 22.0° C. and relative air humidity of 40 to 60%. A dim red light was the sole source of illumination during the dark period. The rats had ad libitum standard chow (Altromin 1324, 10% kcal from fat, energy density 2.85 kcal per g, Altromin GmbH, Lage, Germany) and water. All experiments were approved (permission no. 2007/561-1343) and conducted in accordance with the guidelines of the Animal Experimentation Inspectorate, Ministry of Justice, Denmark.

Simultaneous Real-Time Feeding and Cardiovascular Monitoring in Telemetrized Rats Telemetry Set-Up The rats were implanted at Harlan laboratories, Horst, the Netherlands, with Data Science International (DSI, St. Paul, USA) Physiotel PA-C40 transmitters according to the manufactures description. In brief, the rats were anaesthetized with isoflurane, ventilated, and a laparotomy was performed under aseptic conditions. A pressure catheter was inserted and sealed in place with Vetbond (3M, St. Paul, USA) into the isolated abdominal aorta. Finally, the transmitter was placed on top of the intestines, in parallel to the long axis of the body, and secured to the abdominal wall, where after the abdominal muscle layer and skin was closed with solvable sutures. The animals were allowed full post-surgical recovery before shipment. Blood pressure (systolic and diastolic arterial blood pressure) and heart rate (pulse rate) data were collected at a sampling rate of 500 Hz using Dataquest A.R.T (v.4.3) and Ponemah software (v.5.0) (DSI, St. Paul, USA) using factory-provided calibration values for the individual transmitters and an Ambient Pressure Reference Monitor (DSI, St. Paul, USA) to ensure accurate blood pressure measurements. Data were collected continuously for 48 h and binned in 5 s intervals.

Real-Time Feeding Monitoring in Telemetrized Rats

Upon 2-3 weeks of post-surgery recovery, the rats were transferred to fully automated food intake monitoring cages (HM-2, MBRose, Faaborg, Denmark) modified to simultaneously determine individualized food intake (by microchip, see below) and cardiovascular condition (by telemetry). For combined telemetry analysis, two receivers (RPC-1, Data Sciences International, St. Paul, Minn.) were placed in the bottom of each HM-2 food intake monitoring cages thereby fully covering the cage surface area. The modified HM-2 food intake monitoring cages were placed in a modified ventilated cabinet with lightproof doors and a light kit for cabinet-based control of light-dark cycle (Scanbur BK, Karslunde, Denmark) being similar to that in the holding rooms. Cabinet temperature was 24.0 to 26.0° C. and relative air humidity of 40 to 60%. The animals were habituated to the HM-2 food intake monitoring system for at least 5 days prior to initiation of drug treatment procedures. Prior to re-housing to the fully automated food intake monitoring cages, the rats were subcutaneuosly injected with a microchip (#402575, eVet, Haderslev, Denmark) to simultaneously identify, and in real-time mode to track feeding behavior of each individual animal throughout the entire experiment. Locomotor activity was detected by an integrated infrared sensor placed above the cage. Standard HM-2 control unit settings are reported previously in further details[7]. All drugs and saline vehicle were administered 30 min before dark onset. All rats received the same treatment in each individual experiment, i.e. a parallel study design was used, and a wash-out period of at least 5 days was used between treatments to assure re-establishment of baseline levels of food intake, locomotor activity, heart rate and blood pressure. The home cage was removed from the HM-2 food intake monitoring system during the drug administration procedure and returned immediately after completion of the drug administration, whereupon automated monitoring of feeding behavior and cardiovascular parameters of each individual animal was resumed. Body weight was measured daily. Body weight and microstructural food intake analysis was performed using a data reporting software (HM-View, MBRose, Faaborg, Denmark).

Statistics

Data were fed into a standard graphic and statistical analysis program (GraphPad Prism v.4.03). Body weight data were calculated as absolute values (g) or daily body weight gain relative (control level=100%) to the first day of drug administration (day 0). Body weight gain and food intake were expressed as means±S.E.M of n individual animals. After acquisition of telemetry data, 12-hour means were calculated using Microsoft Excel 2007. Finally, statistical analysis and data presentation (mean±S.E.M.) was performed using GraphPad Prism v.4.03). All data were evaluated using a repeated-measure one-way ANOVA with Tukey's post-hoc test was applied to perform statistical comparisons between treatment groups. A p-value less than 0.05 was considered statistically significant.

Drugs

Tesofensine (8-Azabicyclo[3.2.1]octane,3-[3,4-dichlorophenyl)-2-(ethoxymethyl)-8-methyl-[1R-(2-endo,3-exo)]-2-hydroxy-1,2,3-propanetricarboxylate) is a derivative of an azabicyclooctane citrate, synthesized at the Department of Medicinal Chemistry, NeuroSearch A/S.

Metoprolol and Telmisartan were purchased from Sigma (St. Louis, Mo.). Tesofensine and Metoprolol were dissolved in 0.9% saline solution, whereas Telmisartan was dissolved in 1 N NaOH and subsequently titrated with 1 N HCl to pH 7.4.

All drugs were administered p.o. (1.0 ml/kg). In drug combination experiments, tesofensine and the anti-hypertensive drug were administered simultaneously (<1 min apart) as separate drug solutions.

RESULTS

Effects on Food Intake and Body Weight

Figure 1B:
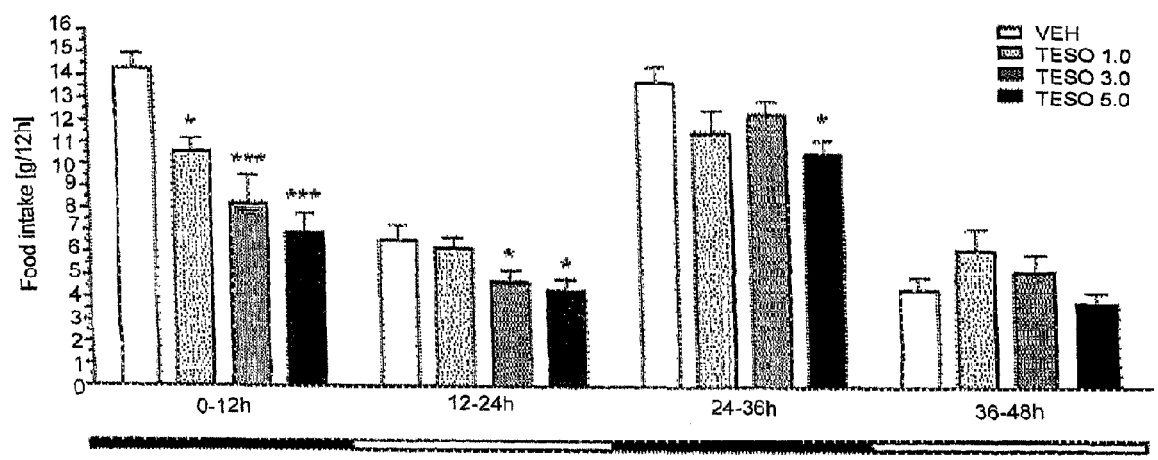
Figure 1C:
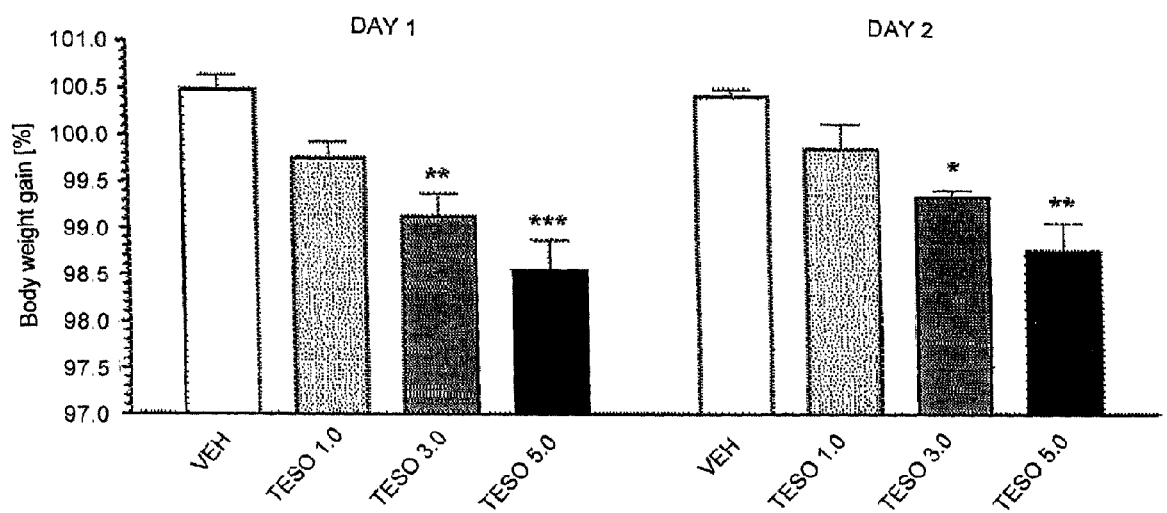
Figure 1D:
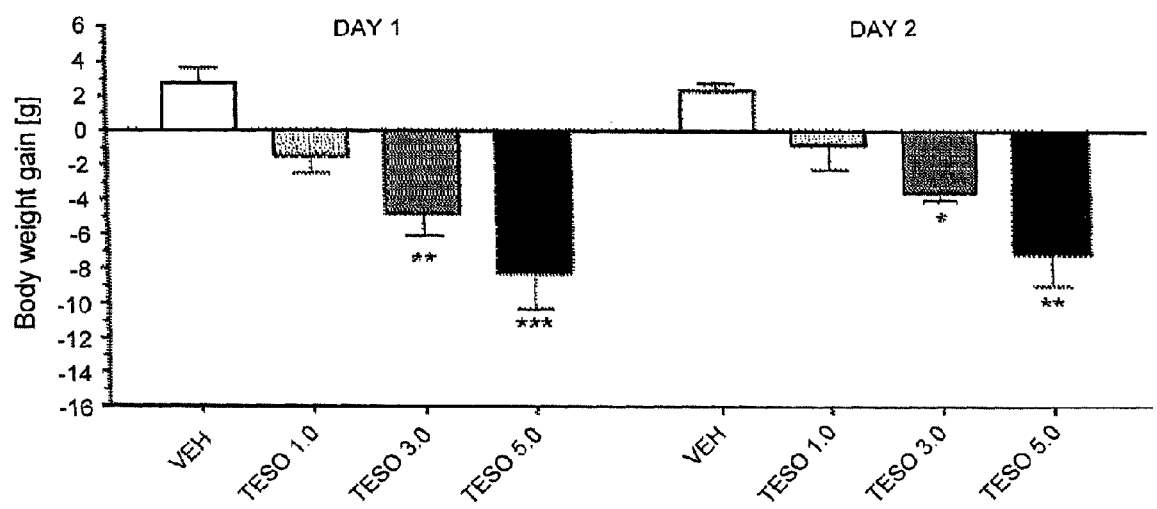
Figure 1E:
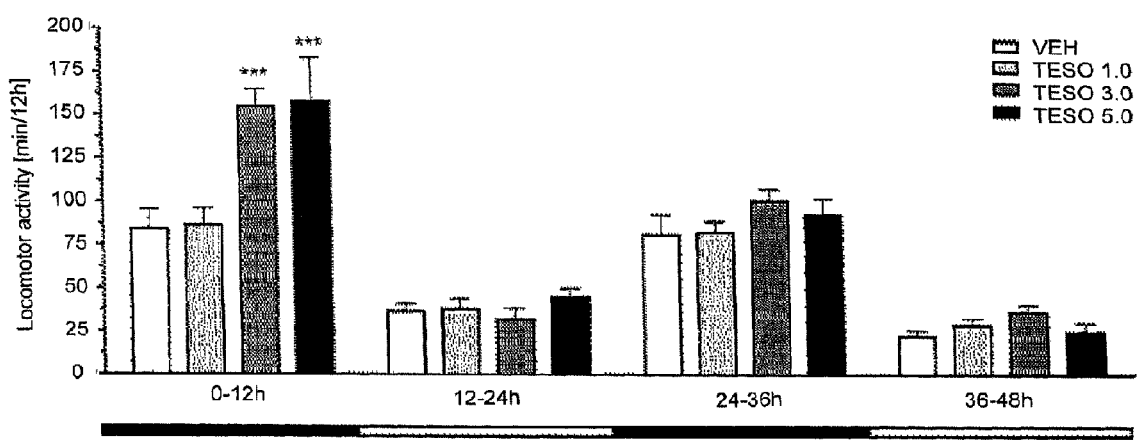

Acute tesofensine administration robustly triggered a reduction of food intake in telemetrized rats (FIGS. 1A and 1B). The food intake in tesofensine-treated rats declined in a dose- and time-dependent fashion with the highest oral dose (5.0 mg/kg) at 12 hours post-dosing reducing food intake to approximately 50% of the control level (p<0.001). The hypophagic effect of tesofensine was sustained for up to 12 hours (all doses), 24 hours (3.0-5.0 mg/kg) and 48 hours (5.0 mg/kg) after dosing, respectively, whereupon food intake returned to baseline levels (FIG. 1B). The hypophagic effect of tesofensine was paralleled by a corresponding dose-dependent reduction in body weight (negative body weight gain) with the highest doses (3.0-5.0 mg/kg) producing a significant net body weight loss of 1.0-1.5% (equivalent to 8-11 g, compared to the body weight of vehicle-treated rats) being evident for at least 48 hours after drug administration (FIGS. 1C and 1D). Tesofensine also dose-dependently induced a significant, albeit short-lasting, increase in locomotor activity in the dose-range of 3.0-5.0 mg/kg (FIG. 1E).

Figure 3A:
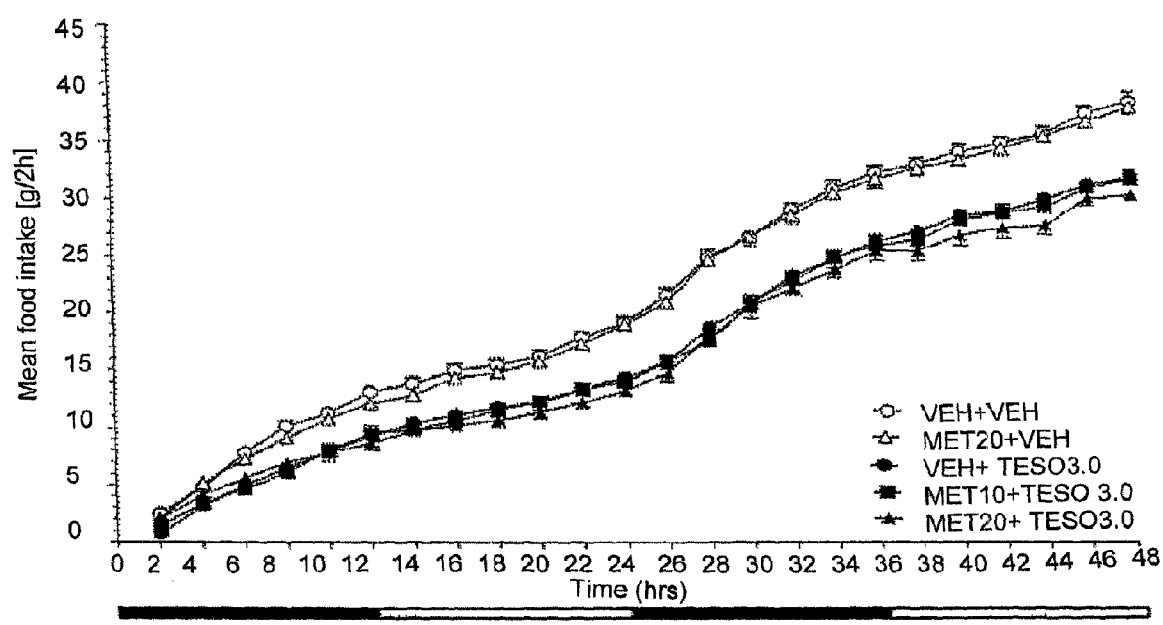
FIGS. 3A-3E show dose-response effects of Metoprolol (given 10, 20 mg/kg, p.o.) in combination with Tesofensine (3.0 mg/kg, p.o.), and that Metoprolol does not affect the hypophagic and weight-lowering effects of tesofensine, but blocks tesofensine-induced locomotor activity in telemetrized rats.
Figure 3B:
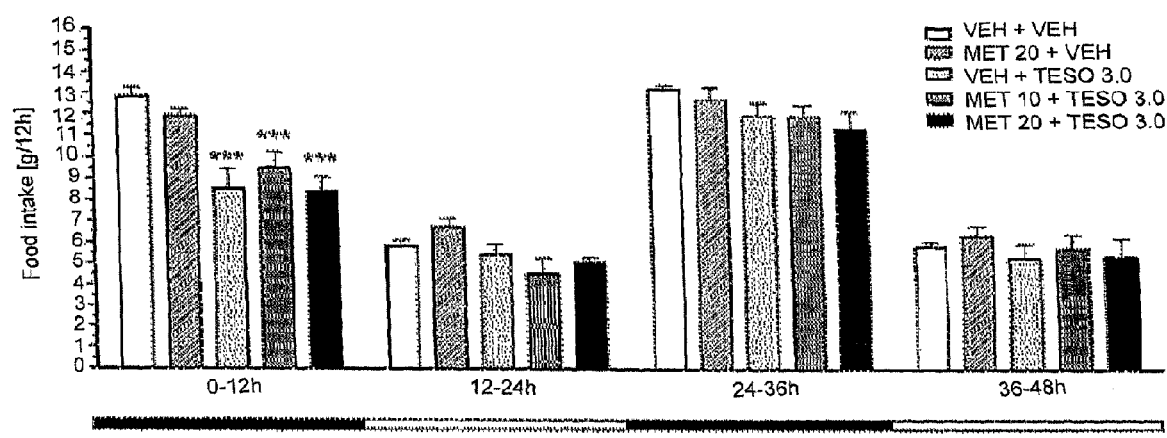
Figure 3C:
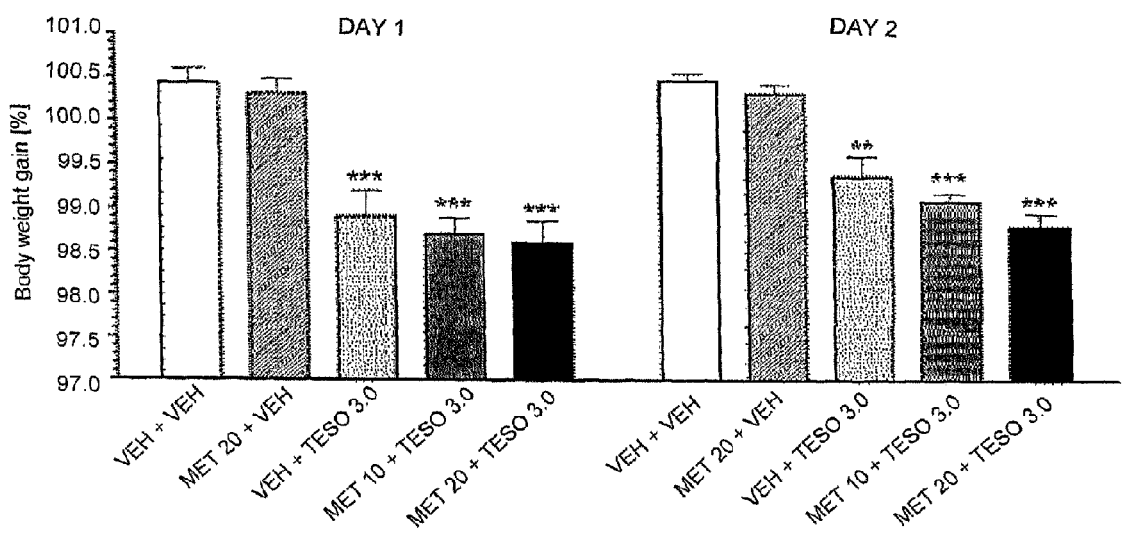
Figure 3D:
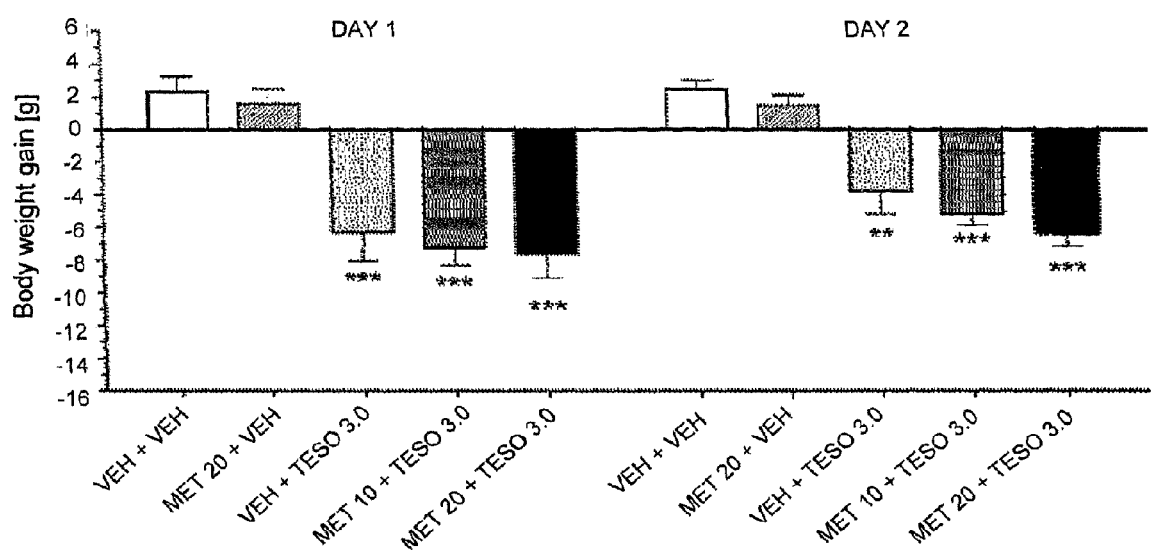
Figure 3E:
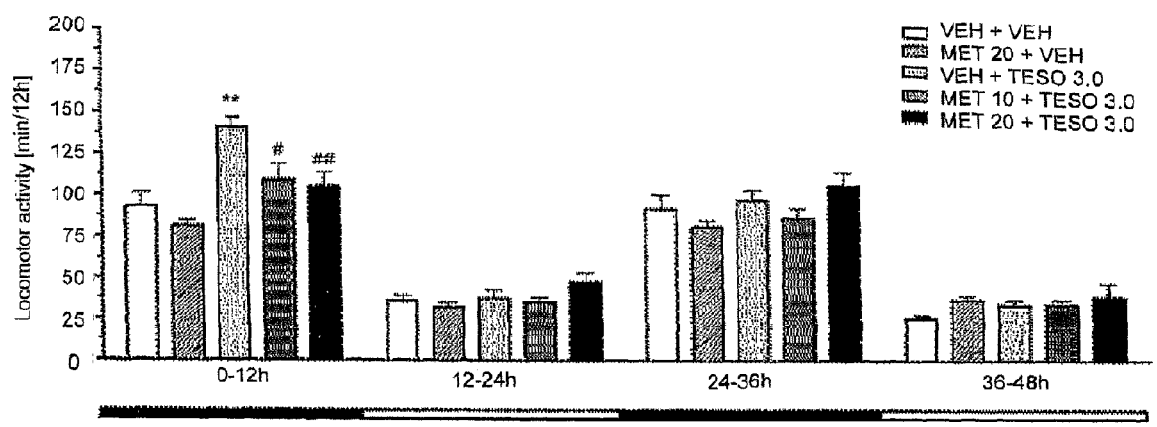
Figure 5A:
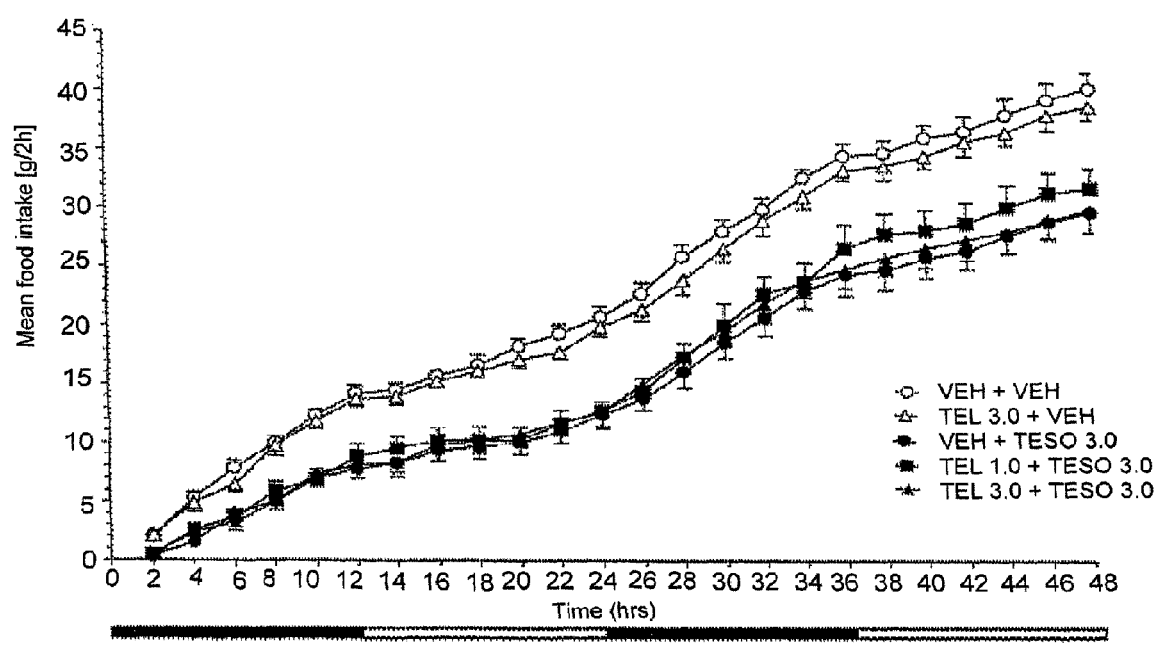
FIGS. 5A-5E show dose-response effects of Telmisartan (1.0, 3.0 mg/kg, p.o.) in combination with tesofensine (3.0 mg/kg, p.o.), and that Telmisartan does not affect the hypophagic and weight-lowering effects of Tesofensine, and has no effect on tesofensine-induced locomotor activity in telemetrized rats.
Figure 5B:
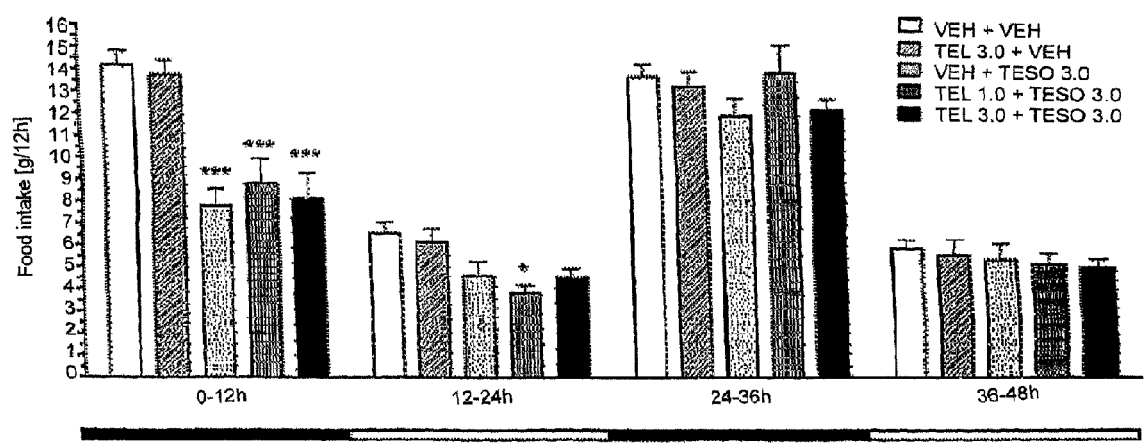
Figure 5C:
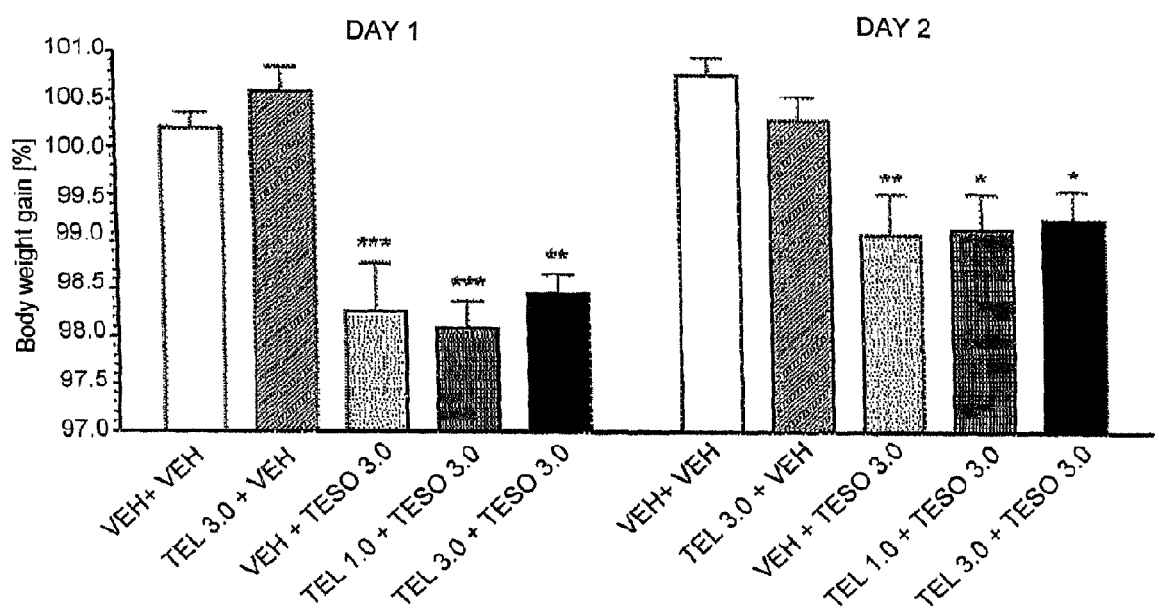
Figure 5D:
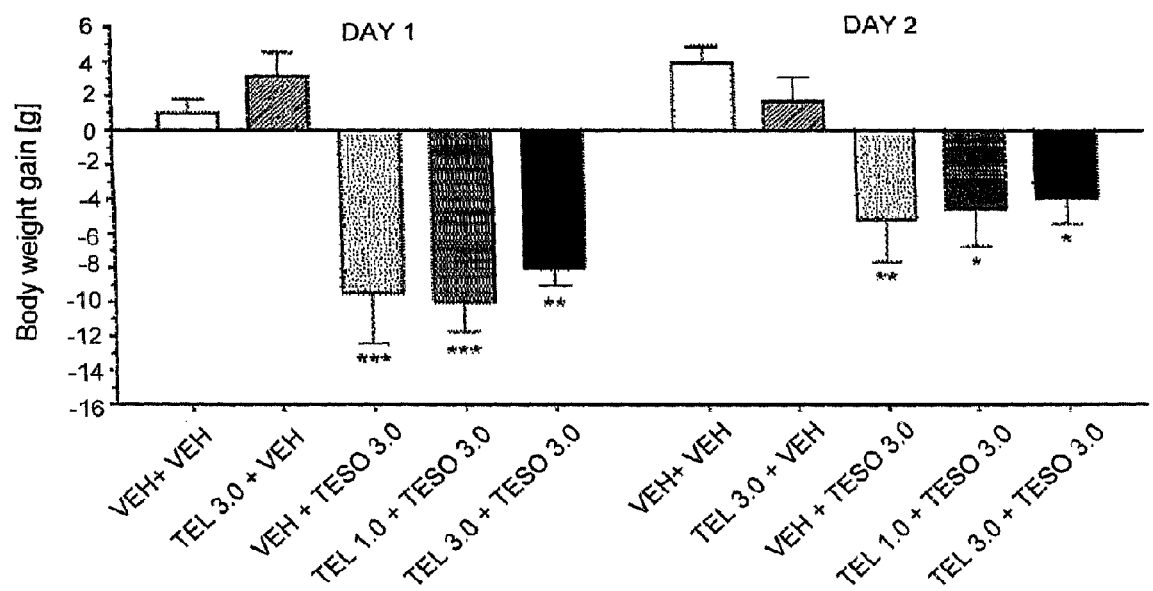
Figure 5E:
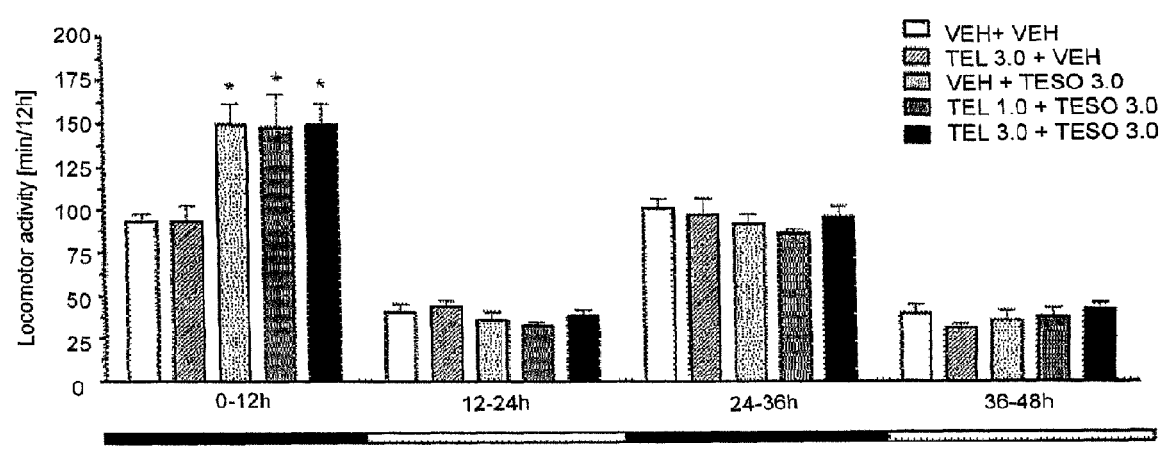

The intermediate dose (3.0 mg/kg) of tesofensine was selected for further characterization in acute drug combination studies with the antihypertensive agents, Metoprolol (FIGS. 3A-3E) and Telmisartan (FIGS. 5A-5E), respectively. These drug interaction studies indicated that neither antihypertensive drug exhibited an effect on food intake or body weight regulation per se, and did also not affect tesofensine-induced reductions in food intake (FIGS. 3A, 3B, 5A, 5B) and body weight (FIGS. 3C, 3D, 5C, 5D). In contrast, Metoprolol (FIG. 3E, p<0.05 compared to tesofensine alone), but not Telmisartan (FIG. 5E, p=0.98 compared to tesofensine alone), completely prevented the locomotor activity inducing effect by tesofensine.

Effects on Cardiovascular Parameters

As expected, the telemetric monitoring of blood pressure and heart rate showed a clear diurnal variation (FIGS. 2A-2C), with higher blood pressure and heart rate observed during the active (nocturnal) period.

Figure 2A:
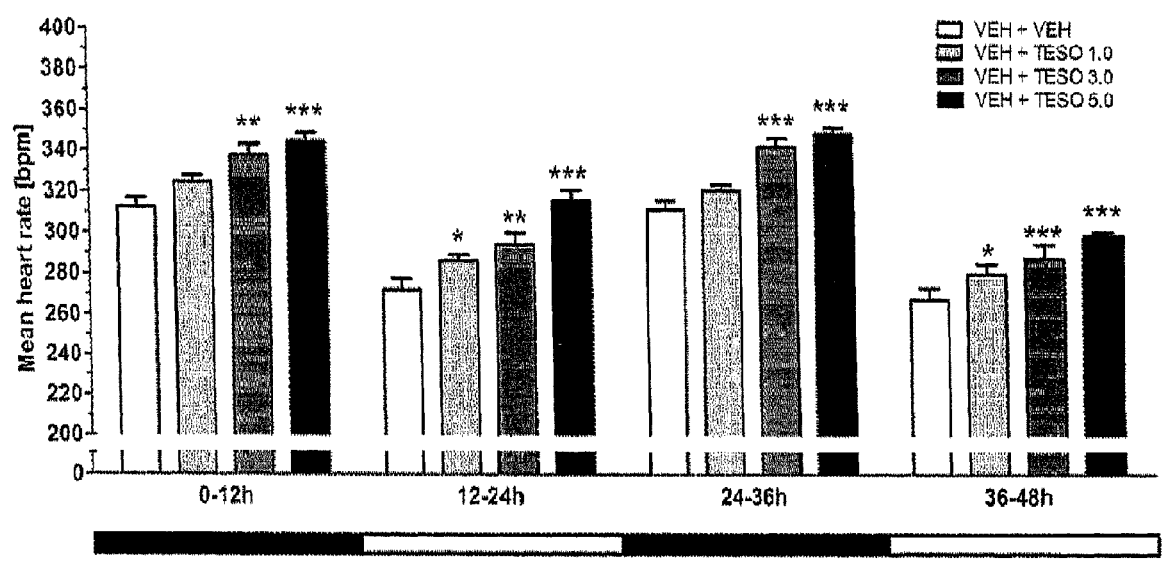
FIGS. 2A-2C show that Tesofensine (given 1.0-5.0 mg/kg, p.o.) dose-dependently elevates heart rate and blood pressure in telemetrized rats.
Figure 2B:
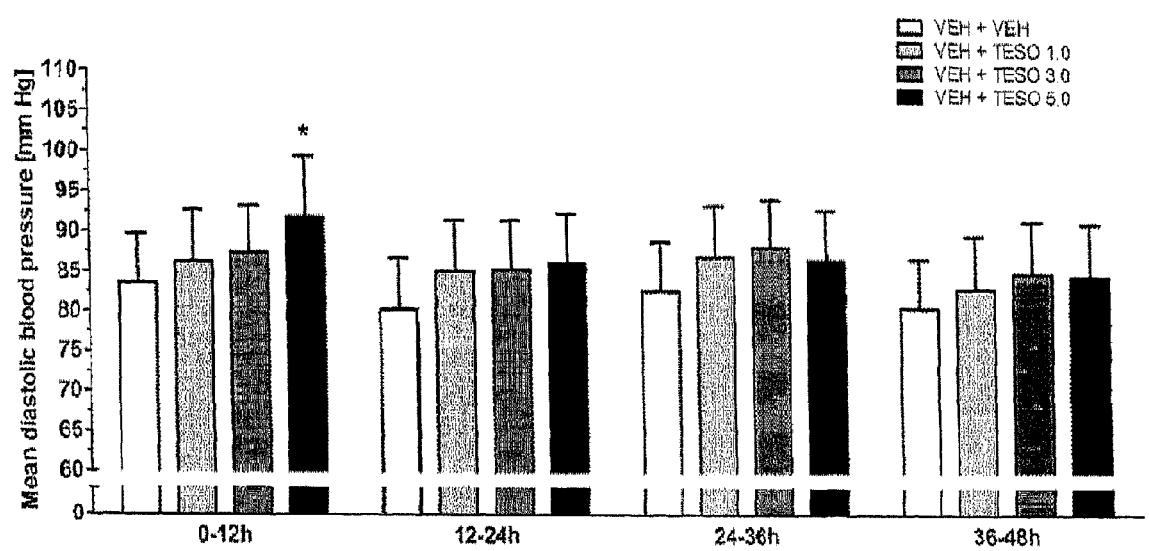
Figure 2C:
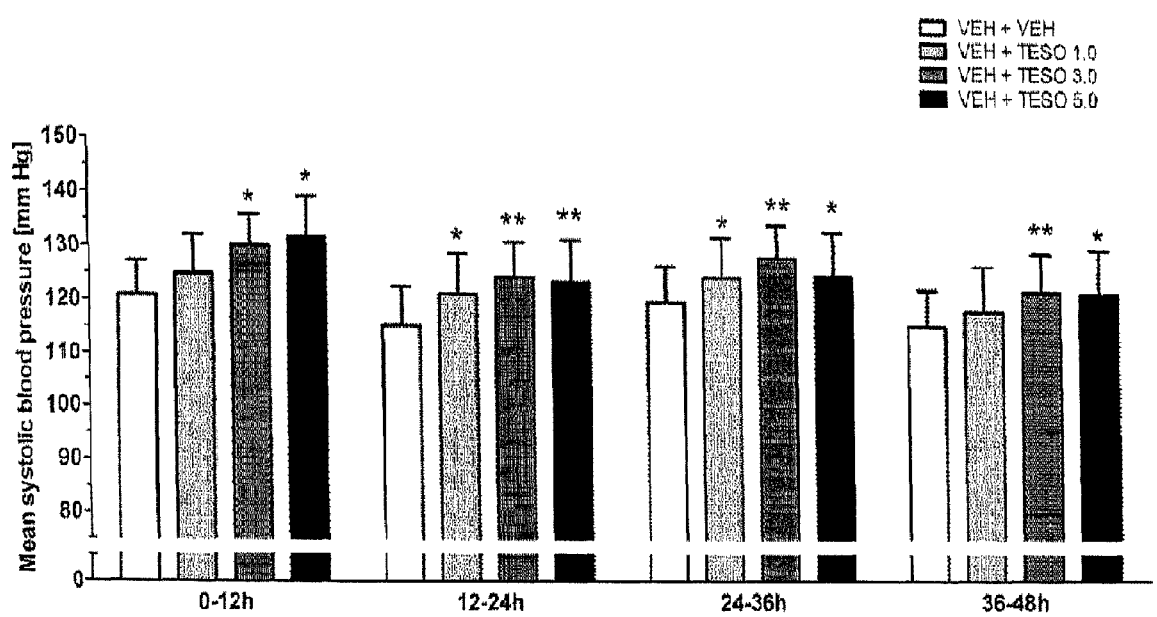

Acute treatment with tesofensine caused a dose-dependent increase in heart rate at all doses tested, lasting for up to 48 hours after treatment (FIG. 2A). Similarly, a dose-dependent modest increase in systolic blood pressure was observed up to 48 hours after drug administration (3.0 mg/kg and 5.0 mg/kg) (FIG. 2C). The effect of 3.0 mg/kg tesofensine on heart rate and systolic blood pressure thereby outlasted the hypophagic effects of 3.0 mg/kg tesofensine. A trend towards a dose-dependent rise in diastolic blood pressure was also observed, although the highest dose did not attain statistical significance (p=0.204, FIG. 2B).

Figure 4A:
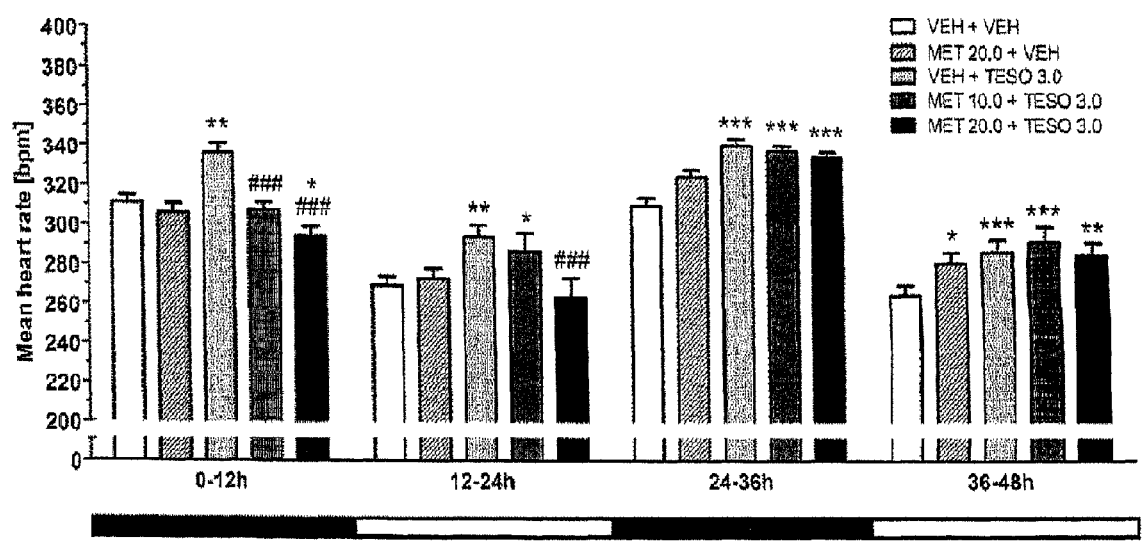
FIGS. 4A-4C show that Metoprolol dose-dependently blocks tesofensine-induced rise in heart rate and blood pressure in telemetrized rats.
Figure 4B:
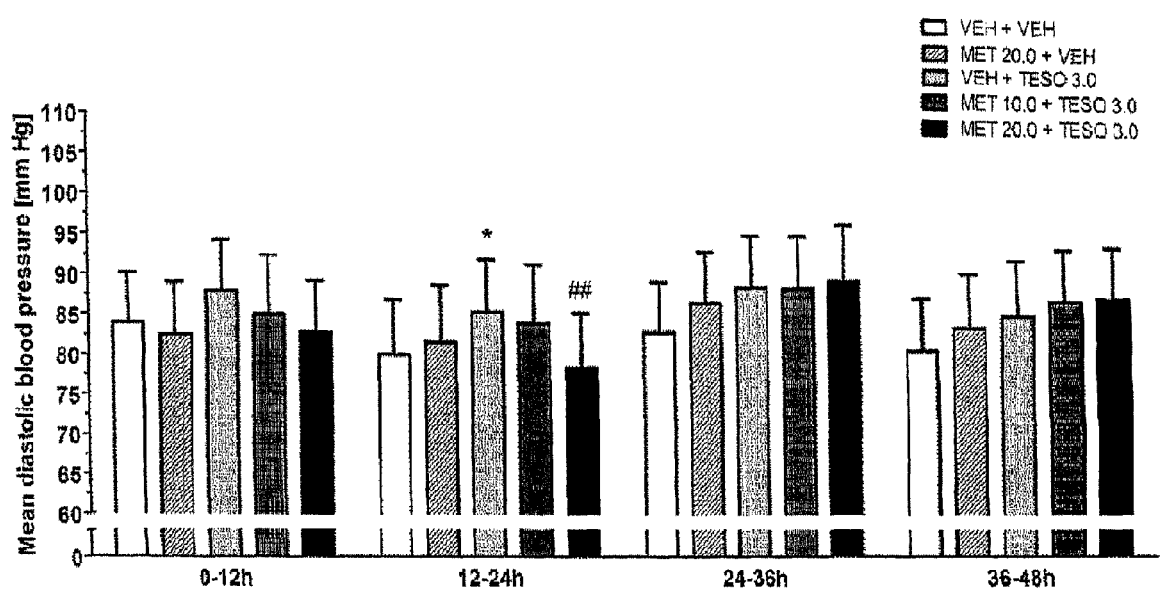
Figure 4C:
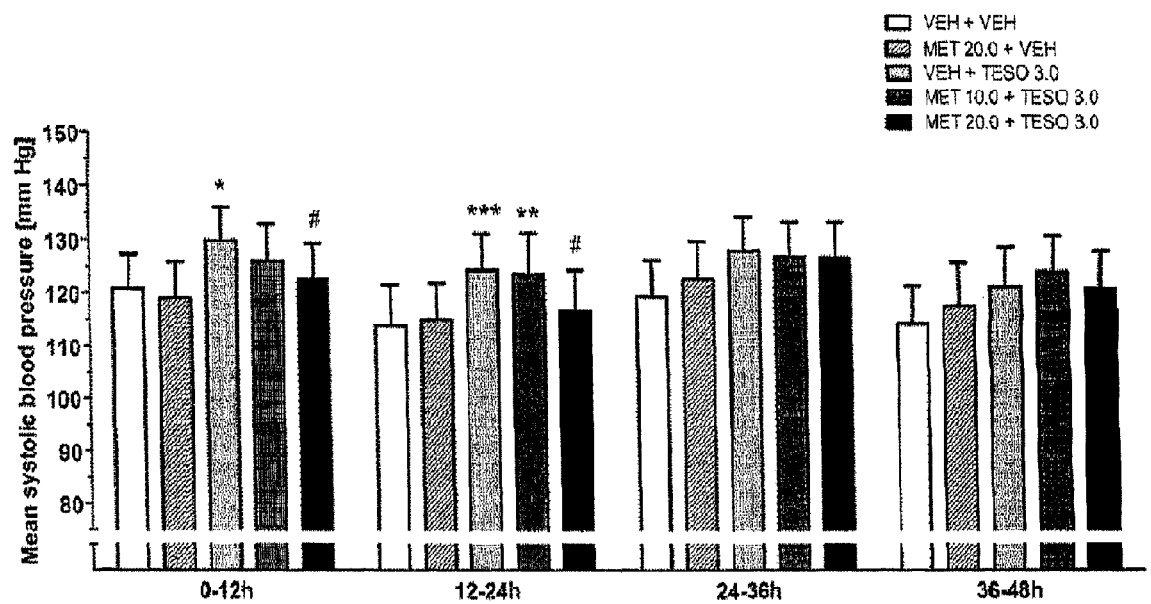

Two combination drug studies were carried out in order to investigate if antihypertensive treatment could prevent or reduce the secondary hypertension and elevated heart rate caused by tesofensine. Co-treatment with tesofensine (3.0 mg/kg) and the $\beta_1$ adrenoceptor antagonist Metoprolol (10 mg/kg and 20 mg/kg) fully reversed tesofensine-induced tachycardia (FIG. 4A). The heart rate lowering effect of Metoprolol was, however, only observed during the first 24 hours after administration, whereas the heart rate was normalized to control levels in the Metoprolol+Tesofensine combination groups (FIG. 4A). The short-lasting effects of Metoprolol reflect the pharmacokinetic properties in the rat. A normalization of the systolic blood pressure was also observed after co-treatment with Metoprolol (20 mg/kg) for up to 24 hours (FIG. 4C). Similarly, the tesofensine-evoked increase in the diastolic pressure during the first light phase (12-24 hours post-treatment) was reversed by co-treatment with Metoprolol (20 mg/kg, FIG. 4B). When administered alone, Metoprolol (20 mg/kg) did not produce any significant effects on diastolic blood pressure in the first 24 hours (FIGS. 4A-4C).

Figure 6A:
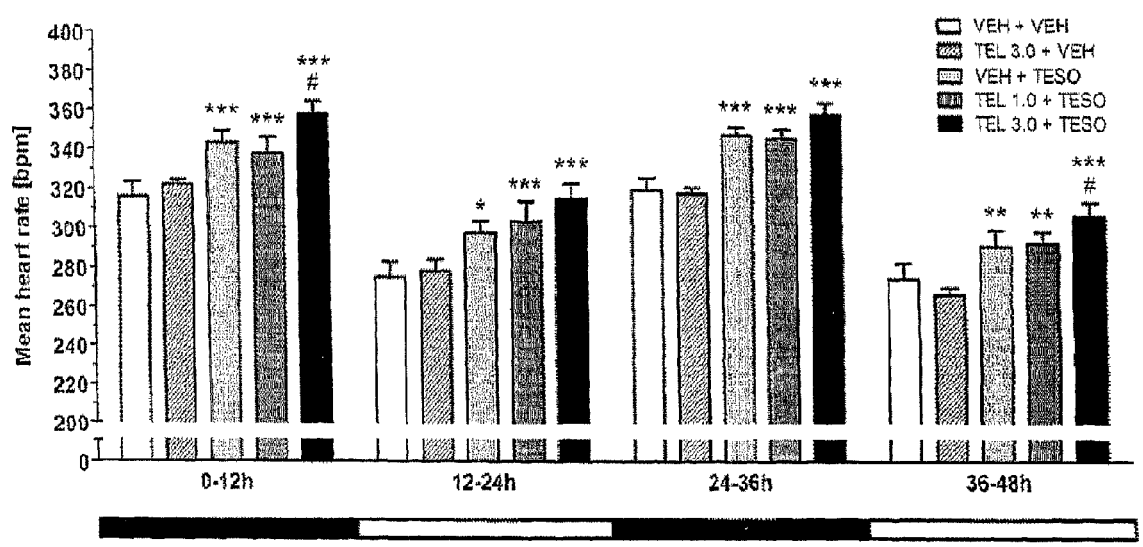
FIGS. 6A-6C show effects of combined Tesofensine+Telmisartan drug treatment on heart rate and blood pressure in telemetrized rats.
Figure 6B:
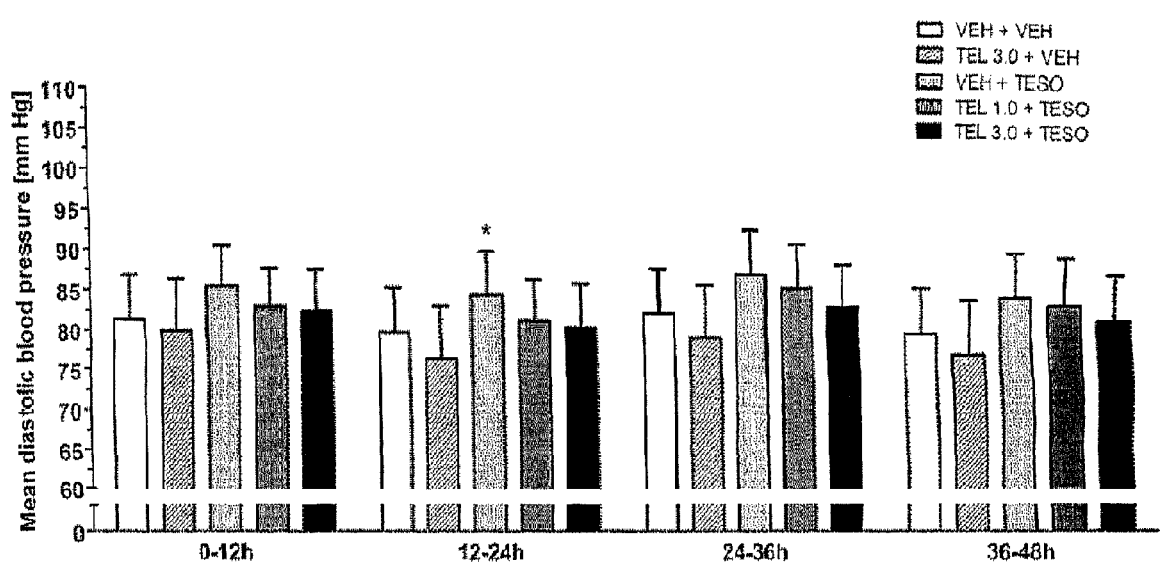
Figure 6C:
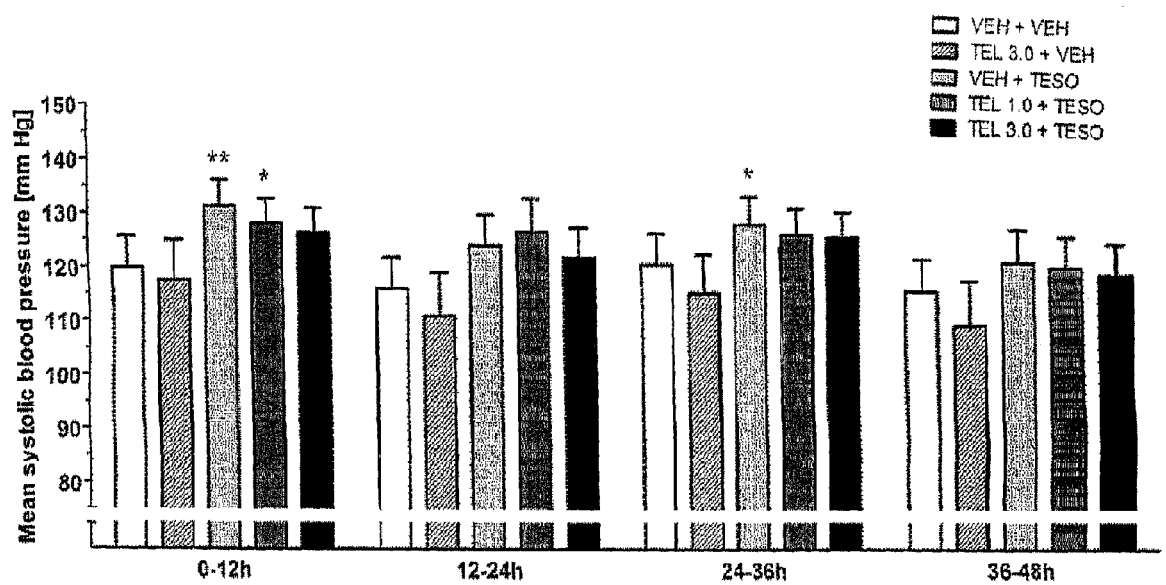

In a subsequent drug combinatorial study, tesofensine and the AT1-receptor antagonist Telmisartan was investigated. As for the Metoprolol study, a similar (3.0 mg/kg) dose of tesofensine was found to significantly increase heart rate. Co-treatment with Telmisartan (1.0 and 3.0) did not revert the rise in heart rate after tesofensine administration, and with the highest dose of Telmisartan combined with tesofensine we observed a significant increase in heart rate as compared to tesofensine administration alone (FIG. 6A). Although co-treatment with Telmisartan was found to attenuate the increases in diastolic and systolic blood pressure produced by Tesofensine, it did not lead to a significant prevention of Tesofensine-induced hypertension (p>0.05, compared to Tesofensine alone, FIGS. 6B, 6C). Telmisartan alone (3.0 mg/kg) had no effect on heart rate and blood pressure (FIGS. 6A-6C).

DISCUSSION

Weight loss is often accompanied by an increase in perceived hunger and appetite sensations, which has been identified as an important predictor of weight relapse, and suppression of appetite function is therefore considered very important for the maintenance of weight loss.

Recent clinical and preclinical reports have indicated that Tesofensine acts as a strong appetite suppressant by triggering satiety and fullness sensations, which is believed to be a key mechanism underlying the robust anti-obesity effect of Tesofensine. Hence, the present data on Tesofensine-induced anorexia in telemetrized rats further supports this view. Tesofensine dose-dependently triggered a rapid hypophagic response lasting for up to 12-48 hours, depending on the dose administered. The long-lasting anorexigenic effect of Tesofensine suggests that the bioactive primary M1 metabolite (also being a triple MRI) of Tesofensine contributed to the hypophagic and weight-lowering effect in rats, as the M1 metabolite exhibits significantly higher steady-state concentrations and longer $T_{1/2}$ in rodents.

In contrast, the human steady-state plasma concentrations of M1 are approximately 60% lower as compared to those of Tesofensine, implying that the contribution of M1 to the overall activity might be lower in humans. In addition, it is suggested that increased energy metabolism may potentially contribute to the robust weight loss induced by Tesofensine. Accordingly, a recent respiratory calorimetry study indicated a moderate rise in fat oxidation and nocturnal thermogenesis after short-term Tesofensine treatment in overweight or moderately obese men. Also, while DIO rats show long-term sustained reductions in body weight during chronic Tesofensine treatment regimens, hypophagia is most pronounced during the first week of treatment followed by a gradual development of tolerance to the anorexigenic effect of Tesofensine, thus being in indirect agreement with the clinical findings.

In the present study, Tesofensine dose-dependently increased locomotor activity during the first 12 hours dark phase, and it may thus be postulated that augmented locomotor activity may have contributed to the weight loss in telemetrized rats, e.g. by causing changes in food-seeking behavior or energy expenditure. However, the hypophagic effect of Tesofensine was more potent and longer lasting (up to 48 hours) as compared to the capacity of Tesofensine to induce locomotor activity (up to 12 hours). In this regard, it is likely that the different temporal pharmacodynamics on food intake and locomotor activity is associated with the pharmacokinetics of Tesofensine.

In comparison to Tesofensine, the M1 metabolite has a longer $T_{1/2}$ (see above) with a four- to five fold lower in vivo potency on dopamine reuptake transporter inhibition, which argues for the metabolite did not contribute significantly to Tesofensine-induced locomotor activity. Also, the evidence that Metoprolol completely prevented the locomotor stimulatory effect of Tesofensine without affecting Tesofensine's efficacy on hypophagia and body weight-reduction, indicates that the moderate increase locomotor activity did not promote a rise in energy metabolism. From these data we infer that locomotor effects had no influence on the appetite suppressing and weight loss effects of Tesofensine. In addition, it may be speculated that Metoprolol antagonized Tesofensine-induced locomotor activity by indirect action on striatal dopaminergic neurotransmission, as various $\beta_1$ blockers are reported to inhibit rat striatal dopamine release.

The preclinical finding of cardiovascular effects of Tesofensine in awake and freely moving rats is in accordance with clinical findings, also showing significant dose-dependent elevations in heart rate at lower dose levels than required to raise diastolic and systolic blood pressure. Notably, the cardiovascular effects outlasted the hypophagic effects following acute administration of Tesofensine. Because Tesofensine and the M1 metabolite show equipotent inhibition of noradrenaline reuptake in vitro, it is likely that the M1 metabolite contributed to the cardiovascular effects of Tesofensine.

Because $\beta_1$ adrenoceptor blockade by Metoprolol co-administration fully prevented the cardiovascular effects of Tesofensine, this strongly indicates that noradrenergic reuptake inhibitory component of Tesofensine is far the most important denominator for the cardiovascular adverse effects of Tesofensine.

Whether Tesofensine would affect blood pressure and heart rate differently in obese rats is not addressed in the present report and must await further studies. It should also be noted that the present observations are restricted to the acute effects of Tesofensine, and do not exclude that the change in cardiovascular parameters in telemetrized rats after chronic Tesofensine treatment may closer mimic clinical findings. Also being in good agreement with clinical and preclinical reports, Tesofensine produced a strong hypophagic response with a corresponding body weight loss in telemetrized rats. Using normal-weight rats fed with chow, the efficacy and temporal pattern of Tesofensine-induced hypophagia and weight reduction observed in the present study is in accordance with similar findings in DIO rats, indicating that acute anti-obesity effects of Tesofensine can also be studied in telemetrized non-obese rats.

Overall, the experimental in vivo settings used in the present study, allowing advanced synchronous monitoring of cardiovascular and food intake parameters in real-time mode, represent a rational and valid methodology for simultaneously studying clinically relevant anti-obesity and vital sign effects of anti-obesity drugs.

Interestingly, the present results suggest a different pharmacodynamic profile of Tesofensine+$\beta_1$ blocker combinational therapy as compared with Sibutramine, a dual serotonin and noradrenaline reuptake inhibitor. Sibutramine exhibits a rather modest weight loss and significant elevates heart rate and blood pressure in obese patients, which constitutes a major concern in the clinical utility of Sibutramine.

A clinical study in obese hypertensive patients indicated that Sibutramine treatment with combined $Ca^{2+}$ channel antagonist+ACE inhibitors or Metoprolol+hydrochlorothiazide treatment, respectively, significantly attenuated Sibutramine's anti-obesity effects. The latter combination most negatively affected Sibutramine's weight-reducing efficacy which may be explained by the common observation that β-blockers can induce weight gain per se.

In contrast, Metoprolol therapy did not significantly interfere with Sibutramine's anti-obesity and metabolic effects in a study on normotensive obese patients, leaving it so far unresolved whether combined $\beta_1$ blocker treatment is feasible to reduce cardiovascular adverse effects of Sibutramine in obese subjects. In this context, it should be noted that anorexigenic effects of Sibutramine are believed to be closely associated with stimulated $\alpha_1$- and $\beta_1$-adrenoceptor function, as Sibutramine-induced hypophagia is antagonized by Prazosin and Metoprolol, respectively.

The implications from these studies may be that anti-obesity drugs with noradrenergic activity will potentially have less anti-obesity efficacy when combined with β-blockers to ameliorate any sympathetic cardiovascular effects. However, the present study suggests that this may not be the case for Tesofensine, because combined treatment with Metoprolol did not affect the anti-obesity effects of Tesofensine. Hence, this observation indicate a clear pharmacodynamic separation between two distinct and important mechanisms of action of Tesofensine, namely the anti-obesity effects associated with $\beta_1$ adrenoceptor stimulation and cardiovascular effects linked to augmented $\beta_1$ adrenoceptor function. The $\beta_1$ adrenoceptor effect of Tesofensine is suggested to be secondary to a blockade of hypothalamic synaptic noradrenaline reuptake leading to inhibition of intrahypothalamic appetite signaling circuits to evoke satiety responses.

In contrast, it is most conceivable that the cardiovascular effects of Tesofensine are being mediated via increased peripheral noradrenergic tonus. Also being in contrast to Sibutramine, the anorexigenic effect of Tesofensine requires stimulation of both $\beta_1$ adrenoceptor and dopamine $D_1$ receptor function to obtain full appetite-suppressing activity in DIO rats, hence indirectly pointing to the possibility that Tesofensine treatment leads to recruitment of dopaminergic neurotransmission. This is relevant, as obese human subjects have indices of impaired central dopaminergic activity thought to instigate overeating behavior to compensate for a lowered hedonic drive.

In healthy human volunteers Tesofensine blocks the neuronal dopamine uptake transporter (DAT) at doses causing weight loss in obese individuals. This finding indicates that the dopamine enhancing effect of tesofensine is involved in mediating the weight reducing effect.

In conclusion, we demonstrate that combined Tesofensine and Metoprolol treatment preserves Tesofensine's anti-obesity efficacy while also preventing elevations in heart rate and blood pressure in rats. These findings invite the possibility that combined antihypertensive treatment with Tesofensine would also be effective in obese patients.

The invention claimed is:
1. A method of reducing food intake by a human comprising:
   administering to the human, 0.1 mg to 1 mg of Tesofensine, or a pharmaceutically acceptable salt thereof, daily in combination with 0.25 mg to 200 mg of Metoprolol, or a pharmaceutically acceptable salt thereof, daily wherein the combination is effective in reducing the food intake by the human and wherein the combination is effective in preventing or alleviating drug-induced cardiovascular side-effects.

2. The method of claim 1, wherein 0.1 mg to about 0.5 mg of the Tesofensine is administered daily.

3. The method of claim 1, wherein 25 mg to 100 mg of the Metoprolol is administered daily.

4. The method of claim 1, wherein the human is a pre-obese human, an obese human, or a morbid obese human.

5. The method of claim 1, wherein the human suffers from a condition selected from the group consisting of over-eating disorders, bulimia nervosa, binge eating disorder, compulsive over-eating, impaired appetite regulation, metabolic syndrome, type 2 diabetes, dyslipidemia, atherosclerosis, and drug-induced obesity.

6. The method of claim 1, wherein the human suffers from type 2 diabetes.

7. A method of reducing body weight of a human comprising:
  administering to the human 0.1 mg to 1 mg of Tesofensine, or a pharmaceutically acceptable salt thereof, daily,
  in combination with 0.25 mg to 200 mg of Metoprolol, or a pharmaceutically acceptable salt thereof, daily;
  wherein the combination is effective to reduce the body weight of the human and wherein the combination is effective in preventing or alleviating drug-induced cardiovascular side-effects.

8. The method of claim 7, wherein 0.1 mg to about 0.5 mg of the Tesofensine is administered daily.

9. The method of claim 7, wherein 25 mg to 100 mg of the Metoprolol is administered daily.

10. The method of claim 7, wherein the obese human is a pre-obese human, an obese human, or a morbid obese human.

11. The method of claim 7, wherein the human suffers from a condition selected from the group consisting of over-eating disorders, bulimia nervosa, binge eating disorder, compulsive over-eating, impaired appetite regulation, metabolic syndrome, type 2 diabetes, dyslipidemia, atherosclerosis, and drug-induced obesity.

12. The method of claim 7, wherein the human suffers from type 2 diabetes.

13. The method of claim 1, wherein the drug-induced cardiovascular side effects are increased heart rate, increased diastolic blood pressure, or increased systolic blood pressure, or a combination thereof.

14. The method of claim 7, wherein the drug-induced cardiovascular side effects are increased heart rate, increased diastolic blood pressure, or increased systolic blood pressure, or a combination thereof.

* * * * *